(12) United States Patent
Negishi

(10) Patent No.: US 11,576,648 B2
(45) Date of Patent: Feb. 14, 2023

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Mitsuru Negishi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 242 days.

(21) Appl. No.: 16/940,913

(22) Filed: Jul. 28, 2020

(65) Prior Publication Data
US 2020/0359993 A1 Nov. 19, 2020

Related U.S. Application Data

(63) Continuation of application No. PCT/JP2019/008570, filed on Mar. 5, 2019.

(30) Foreign Application Priority Data

Mar. 5, 2018 (JP) .............................. JP2018-038661

(51) Int. Cl.
*A61B 8/10* (2006.01)
*G06T 7/64* (2017.01)
(Continued)

(52) U.S. Cl.
CPC .............. *A61B 8/10* (2013.01); *A61B 8/4472* (2013.01); *A61B 8/5223* (2013.01); *A61B 8/54* (2013.01);
(Continued)

(58) Field of Classification Search
CPC ....... A61B 8/10; A61B 8/5223; A61B 8/0808; A61B 8/08; A61B 8/0833; A61B 8/085;
(Continued)

(56) References Cited

U.S. PATENT DOCUMENTS 5,867,249 A 2/1999 Ichiki et al.
7,203,351 B1* 4/2007 Swindale ............. A61B 3/0025
351/212
(Continued)

FOREIGN PATENT DOCUMENTS

CA 2147149 A1 4/1994
JP H08-502188 A 3/1996
(Continued)

OTHER PUBLICATIONS

International Search Report issued in PCT/JP2019/008570; dated May 28, 2019.
(Continued)

*Primary Examiner* — Carolyn A Pehlke
(74) *Attorney, Agent, or Firm* — Studebaker & Brackett PC

(57) ABSTRACT

An ultrasound diagnostic apparatus 1 includes an image acquisition unit 8 that transmits an ultrasound beam from an ultrasound probe 18 to a subject to acquire an ultrasound image, an optic nerve recognition unit 9 that performs image analysis on the ultrasound image acquired by the image acquisition unit 8 to recognize an optic nerve of the subject, an optic nerve evaluation unit 10 that evaluates a shape of the optic nerve of the subject recognized by the optic nerve recognition unit 9 on the basis of an anatomical structure, and an operation guide unit 12 that guides a user to operate the ultrasound probe 18 so as to acquire an ultrasound image for measurement of the optic nerve of the subject on the basis of an evaluation result obtained by the optic nerve evaluation unit 10.

14 Claims, 6 Drawing Sheets

(51) Int. Cl.
A61B 8/00 (2006.01)
A61B 8/08 (2006.01)
G06T 7/00 (2017.01)

(52) U.S. Cl.
CPC .......... *A61B 8/565* (2013.01); *G06T 7/0014* (2013.01); *G06T 7/64* (2017.01); *G06T 2207/10132* (2013.01); *G06T 2207/30041* (2013.01)

(58) Field of Classification Search
CPC . A61B 8/46; A61B 8/461; G06T 2207/10132; G06T 2207/30041; G06T 7/0012; G06T 7/0014; G06T 7/64; G06T 7/60
See application file for complete search history.

(56) References Cited

U.S. PATENT DOCUMENTS

| | | | |
|---|---|---|---|
| 8,672,851 B1 | 3/2014 | Quirk et al. | |
| 2011/0137182 A1 | 6/2011 | Bellezza et al. | |
| 2015/0051489 A1* | 2/2015 | Caluser | A61B 8/5207 600/440 |
| 2016/0000367 A1 | 1/2016 | Lyon | |
| 2017/0262982 A1* | 9/2017 | Pagoulatos | A61B 8/469 |
| 2018/0368679 A1* | 12/2018 | An | A61B 3/0025 |

FOREIGN PATENT DOCUMENTS

| | | |
|---|---|---|
| JP | 2006-061196 A | 3/2006 |
| JP | 2014-039884 A | 3/2014 |
| JP | 2015-188467 A | 11/2015 |
| RU | 2 472 472 C1 | 1/2013 |

OTHER PUBLICATIONS

International Preliminary Report on Patentability and Written Opinion issued in PCT/JP2019/008570; dated Sep. 8, 2020.

Gabriella Csurka et al.; "Visual Categorization with Bags of Keypoints"; Proc. Of ECCV Workshop on Statistical Learning in Computer Vision; 2004; pp. 59-74.

Alex Krizhevsky et al.; "ImageNet Classification with Deep Convolutional Neural Networks"; Advances in Neural Information Processing Systems 25; 2012; pp. 1106-1114.

Venkatakrishna Rajajee et al.,"Optic Nerve Ultrasound for the Detection of Raised Intracranial Pressure", Neurocritical Care, pp. 506-515, vol. 15, No. 3, Jul. 19, 2011, Humana Press Inc, New York.

Yanamandra Uday et al., "Comparison of Optic Nerve Sheath Diameter between both eyes: A Bedside Ultrasonography Approach", Indian journal of critical care medicine, pp. 150-153, Mar. 1, 2018, India.

Del Saz-Saucedo Pablo et al., "Sonographic Assessment of the Optic Nerve Sheath Diameter in the Diagnosis of Idiopathic Intracranial Hypertension", Journal of the Neurological Sciences, pp. 122-127, vol. 361, Dec. 21, 2015, Elsevier Scientific Publishing Co, NL.

Hossein-Nejad et al., "Emergency Ocular Ultrasonography to Measure Optic Nerve Sheath Diameter", ACEP Now, total 4 pages, Jun. 20, 2017, https://www.https://www.https://www.acepnow.com/article/emergency-ocular-ultrasonography-measure-optic-nerve-sheath-diameter/?singlepage=1&theme=print-friendly.

Jochen Bäuerle et al., "Reproducibility and Accuracy of Optic Nerve Sheath Diameter Assessment Using Ultrasound Compared to Magnetic Resonance Imaging", BMC Neurology, p. 187(1-6), vol. 13, No. 1, Dec. 1, 2013, Biomed Central Ltd, London, GB.

Hassen Getaw Worku et al., "Accuracy of Optic Nerve Sheath Diameter Measurement by Emergency Physicians Using Bedside Ultrasound", The Journal of Emergency Medicine, pp. 450-457, vol. 48, No. 4, Dec. 9, 2014, Pergamon Press, New York.

The extended European search report issued by the European Patent Office dated Apr. 8, 2021, which corresponds to European Patent Application No. 19763406.6-1126 and is related to U.S. Appl. No. 16/940,913.

An Office Action mailed by China National Intellectual Property Administration dated Nov. 23, 2022, which corresponds to Chinese Patent Application No. 201980015032.X and is related to U.S. Appl. No. 16/940,913; with partial English translation.

\* cited by examiner

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2019/008570 filed on Mar. 5, 2019, which claims priority under 35 U.S.C. § 119(a) to Japanese Patent Application No. 2018-038661 filed on Mar. 5, 2018. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more specifically to an ultrasound diagnostic apparatus for performing optic nerve measurement and a method for controlling the ultrasound diagnostic apparatus.

2. Description of the Related Art

Ultrasound diagnostic apparatuses are known in the related art as apparatuses for obtaining an image of the inside of a subject. An ultrasound diagnostic apparatus typically includes an ultrasound probe including a vibrator array in which a plurality of elements are arrayed. While the ultrasound probe is in contact with the body surface of the subject, an ultrasound beam is transmitted from the vibrator array to the inside of the subject, and an ultrasound echo from the subject is received by the vibrator array to acquire element data. Further, the ultrasound diagnostic apparatus electrically processes the obtained element data and generates an ultrasound image of the corresponding site of the subject.

An ultrasound diagnostic apparatus for automatically performing optic nerve measurement using the ultrasound diagnostic apparatus described above is disclosed in, for example, U.S. Pat. No. 8,672,851B.

SUMMARY OF THE INVENTION

When an ultrasound image of an optic nerve is to be captured, due to a deviation in the orientation of the eyeballs of the subject, an image of a curved optic nerve is sometimes captured. To address this, for example, a user can give an instruction to the subject not to cause a deviation in the orientation of the eyeballs to allow the subject to correct the orientation of the eyeballs. However, the subject with impaired consciousness or the like is not able to correct the orientation of the eyeballs in response to an instruction given to the subject. The ultrasound diagnostic apparatus disclosed in U.S. Pat. No. 8,672,851B does not take into account the deviation in the orientation of the eyeballs, and it may therefore be difficult to acquire an ultrasound image for suitably measuring the optic nerve of the subject.

Typically, in the measurement of the optic nerve, it is desirable to acquire an ultrasound image, with an ultrasound probe oriented in a direction extending along the central axis of the optic nerve. However, operating the ultrasound probe in this way to acquire a desired ultrasound image requires the user's skill. If a user who is unfamiliar with the ultrasound diagnostic apparatus operates the ultrasound probe, for example, an ultrasound image in which the optic nerve appears to be largely tilted relative to the eyeball axis may be acquired. Accordingly, it may be difficult to acquire an ultrasound image for suitably measuring the optic nerve of the subject.

The present invention has been made to solve the problems of the related art described above, and it is an object of the present invention to provide an ultrasound diagnostic apparatus and a method for controlling the ultrasound diagnostic apparatus that enable accurate measurement of the optic nerve of the subject, regardless of the user.

To achieve the object described above, an ultrasound diagnostic apparatus of the present invention includes an image acquisition unit that transmits an ultrasound beam from an ultrasound probe to a subject to acquire an ultrasound image, an optic nerve recognition unit that performs image analysis on the ultrasound image acquired by the image acquisition unit to recognize an optic nerve of the subject, an optic nerve evaluation unit that evaluates a shape of the optic nerve of the subject recognized by the optic nerve recognition unit, and an operation guide unit that guides a user to operate the ultrasound probe so as to acquire an ultrasound image for measurement of the optic nerve of the subject on the basis of an evaluation result obtained by the optic nerve evaluation unit.

The optic nerve evaluation unit can evaluate whether the optic nerve of the subject is curved with a degree of curvature greater than a determined degree of curvature.

Further, when the optic nerve evaluation unit evaluates that the optic nerve of the subject is curved with a degree of curvature greater than the determined degree of curvature, the operation guide unit can guide the user to operate the ultrasound probe so as to perform measurement on an opposite eye.

Further, the ultrasound diagnostic apparatus can further include a reference data memory that stores reference data regarding an optic nerve of only one of left and right eyes that is curved with a degree of curvature greater than the determined degree of curvature, and when the optic nerve evaluation unit evaluates that an optic nerve of the opposite eye is curved with a degree of curvature greater than the determined degree of curvature, the operation guide unit can present to the user a measurement result of the optic nerve of the subject, the measurement result being estimated on the basis of the reference data stored in the reference data memory.

Further, the reference data memory preferably stores the reference data that is collected from previous result data.

Further, the operation guide unit can estimate a measurement result obtained assuming that the degree of curvature of the optic nerve of the subject is less than or equal to the determined degree of curvature, by using a regression line obtained from the previous result data.

Alternatively, the operation guide unit can estimate the measurement result of the optic nerve of the subject through machine learning using an image feature value.

Further, when the optic nerve evaluation unit evaluates that the degree of curvature of the optic nerve of the subject is less than or equal to the determined degree of curvature, the optic nerve evaluation unit can further evaluate whether the optic nerve of the subject is tilted with a slope greater than a determined slope.

Further, when the optic nerve evaluation unit evaluates that the degree of curvature of the optic nerve of the subject is less than or equal to the determined degree of curvature and that the optic nerve of the subject is tilted with a slope greater than the determined slope, the operation guide unit can guide the user to operate the ultrasound probe so as to reduce the slope of the optic nerve of the subject.

Further, the ultrasound diagnostic apparatus can further include a diagnostic apparatus main body having the ultrasound probe and the image acquisition unit, and an external processing apparatus having the optic nerve recognition unit, the optic nerve evaluation unit, and the operation guide unit, and the diagnostic apparatus main body and the external processing apparatus can be connected to each other via communication.

A method for controlling an ultrasound diagnostic apparatus of the present invention includes transmitting an ultrasound beam from an ultrasound probe to a subject to acquire an ultrasound image; performing image analysis on the acquired ultrasound image to recognize an optic nerve of the subject; evaluating a shape of the recognized optic nerve of the subject; and guiding a user to operate the ultrasound probe so as to acquire an ultrasound image for measurement of the optic nerve of the subject on the basis of an evaluation result.

According to the present invention, an optic nerve evaluation unit that evaluates a shape of an optic nerve of a subject recognized by an optic nerve recognition unit, and an operation guide unit that guides a user to operate an ultrasound probe so as to acquire an ultrasound image for measurement of the optic nerve of the subject on the basis of an evaluation result obtained by the optic nerve evaluation unit are included. This enables accurate measurement of the optic nerve of the subject, regardless of the user.

DESCRIPTION OF THE PREFERRED EMBODIMENTS

The following describes embodiments of this invention with reference to the accompanying drawings.

Embodiment 1

Figure 1:
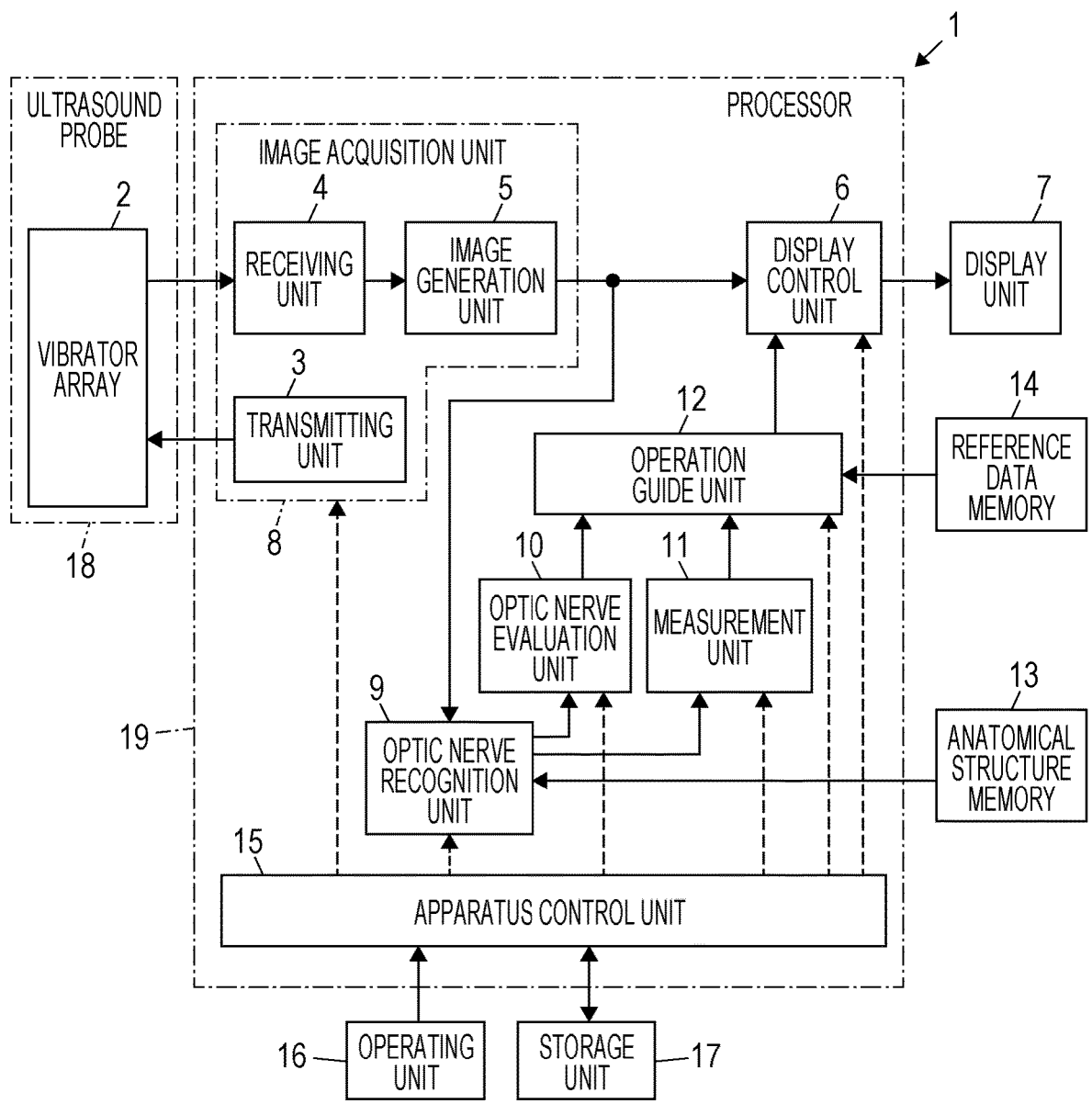
FIG. 1 is a block diagram illustrating a configuration of an ultrasound diagnostic apparatus according to Embodiment 1 of the present invention.

FIG. 1 illustrates a configuration of an ultrasound diagnostic apparatus 1 according to Embodiment 1 of the present invention. As illustrated in FIG. 1, the ultrasound diagnostic apparatus 1 includes a vibrator array 2, and the vibrator array 2 is connected to a transmitting unit 3 and a receiving unit 4. The receiving unit 4 is sequentially connected to an image generation unit 5, a display control unit 6, and a display unit 7. The transmitting unit 3, the receiving unit 4, and the image generation unit 5 constitute an image acquisition unit 8. The image generation unit 5 is further connected to an optic nerve recognition unit 9, and the optic nerve recognition unit 9 is connected to an optic nerve evaluation unit 10, a measurement unit 11, and an anatomical structure memory 13. The optic nerve evaluation unit 10 and the measurement unit 11 are further connected to an operation guide unit 12, and the operation guide unit 12 is connected to the display control unit 6 and a reference data memory 14.

Further, the display control unit 6, the image acquisition unit 8, the optic nerve recognition unit 9, the optic nerve evaluation unit 10, the measurement unit 11, and the operation guide unit 12 are connected to an apparatus control unit 15, and the apparatus control unit 15 is connected to an operating unit 16 and a storage unit 17. The apparatus control unit 15 and the storage unit 17 are connected so as to enable two-way exchange of information.

The vibrator array 2 is included in an ultrasound probe 18. The display control unit 6, the image acquisition unit 8, the optic nerve recognition unit 9, the optic nerve evaluation unit 10, the measurement unit 11, the operation guide unit 12, and the apparatus control unit 15 constitute a processor 19.

The vibrator array 2 of the ultrasound probe 18 illustrated in FIG. 1 has a plurality of vibrators that are arrayed one-dimensionally or two-dimensionally. Each of these vibrators transmits an ultrasound wave in accordance with a drive signal supplied from the transmitting unit 3 and outputs a reception signal upon receipt of an ultrasound echo from the subject. Each vibrator is constructed by, for example, forming electrodes at both ends of a piezoelectric body composed of a piezoelectric ceramic typified by PZT (Lead Zirconate Titanate), a polymeric piezoelectric element typified by PVDF (Poly Vinylidene Di Fluoride), a piezoelectric single crystal typified by PMN-PT (Lead Magnesium Niobate-Lead Titanate), or the like.

The transmitting unit 3 of the image acquisition unit 8 includes, for example, a plurality of pulse generators, and supplies to the plurality of vibrators of the vibrator array 2 respective drive signals whose amounts of delay are adjusted so that the ultrasound waves transmitted from the plurality of vibrators form an ultrasound beam on the basis of a transmission delay pattern selected in accordance with a control signal from the apparatus control unit 15. In this manner, when a pulsed or continuous-wave voltage is applied to the electrodes of the plurality of vibrators of the vibrator array 2, the piezoelectric bodies expand and contract. Pulsed or continuous-wave ultrasound waves are generated from the respective vibrators, and a composite wave of these ultrasound waves forms an ultrasound beam.

The transmitted ultrasound beam is reflected from, for example, a target such as a site of the subject and propagates toward the vibrator array 2 of the ultrasound probe 18. The ultrasound echo propagating toward the vibrator array 2 in this manner is received by the respective vibrators of the vibrator array 2. At this time, upon receipt of the propagating ultrasound echo, the respective vibrators of the vibrator array 2 expand and contract to generate electrical signals, and these electrical signals are output to the receiving unit 4.

Figure 2:
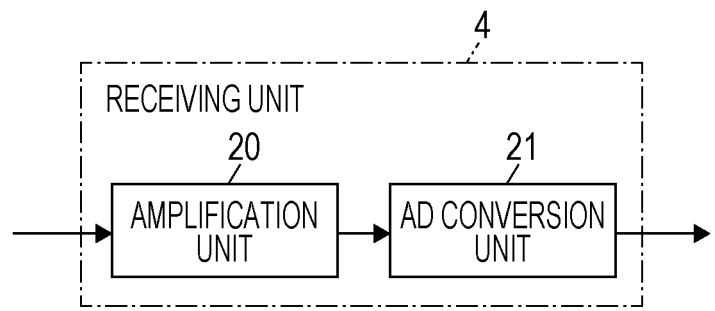
FIG. 2 is a block diagram illustrating an internal configuration of a receiving unit in Embodiment 1 of the present invention.

The receiving unit 4 of the image acquisition unit 8 processes the reception signals output from the vibrator array 2 in accordance with a control signal from the apparatus control unit 15. As illustrated in FIG. 2, the receiving unit 4 has a configuration in which an amplification unit 20 and an AD (Analog Digital) conversion unit 21 are connected in series. The amplification unit 20 amplifies the reception signals input from the respective elements of the vibrator array 2 and transmits the amplified reception signals to the AD conversion unit 21. The AD conversion unit 21 converts the reception signals transmitted from the amplification unit 20 into digital data and sends the data to the image generation unit 5 of the image acquisition unit 8.

Figure 3:
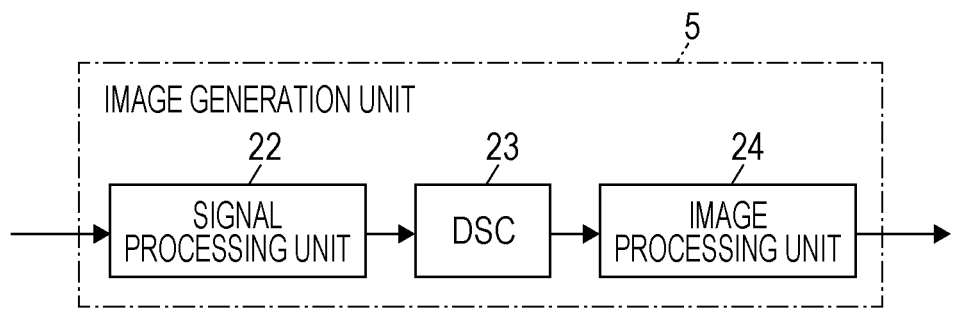
FIG. 3 is a block diagram illustrating an internal configuration of an image generation unit in Embodiment 1 of the present invention.

As illustrated in FIG. 3, the image generation unit 5 of the image acquisition unit 8 has a configuration in which a signal processing unit 22, a DSC (Digital Scan Converter) 23, and an image processing unit 24 are connected in series. The signal processing unit 22 performs reception focus processing in which the pieces of data of the reception signals are given respective delays on the basis of a reception delay pattern selected in accordance with a control signal from the apparatus control unit 15 and are added together (phasing addition). Through the reception focus processing, a sound ray signal in which the focus of the ultrasound echo is narrowed to a single scan line is generated. Further, the signal processing unit 22 corrects the generated sound ray signal for attenuation caused by the propagation distance in accordance with the depth of the position at which the ultrasound wave is reflected, and then performs envelope detection processing to generate a B-mode image signal indicating tissue in the subject. The B-mode image signal generated in this way is output to the DSC 23.

The DSC 23 of the image generation unit 5 performs raster conversion to convert the B-mode image signal into an image signal based on a typical television signal scanning method. The image processing unit 24 of the image generation unit 5 performs various necessary image processing operations, such as brightness correction, gradation correction, sharpness correction, and color correction, on the image data obtained by the DSC 23, and then outputs the B-mode image to the display control unit 6 and the optic nerve recognition unit 9.

Figure 4:
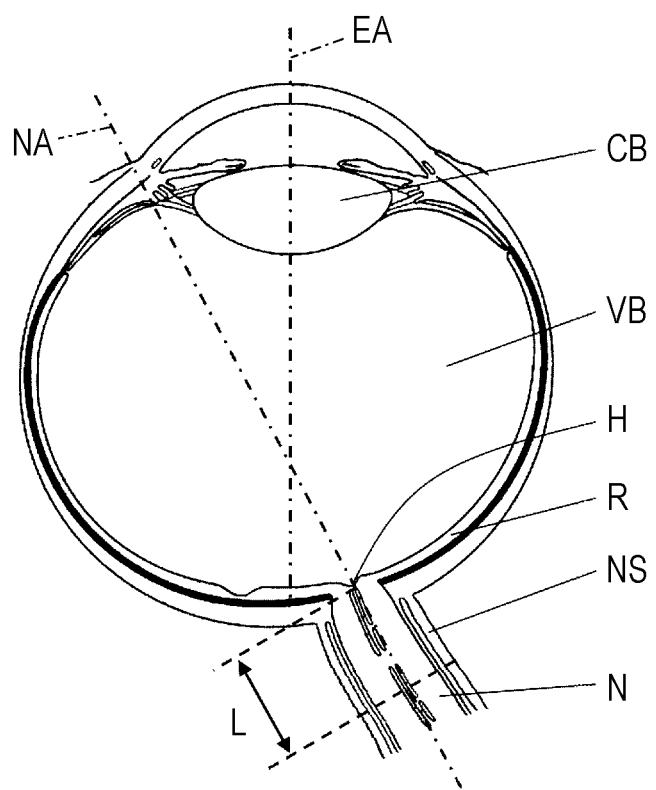
FIG. 4 is a schematic diagram illustrating neighboring anatomical structures of the optic nerve.

The anatomical structure memory 13 of the ultrasound diagnostic apparatus 1 stores information regarding neighboring anatomical structures of an optic nerve N. Specifically, as illustrated in FIG. 4, the anatomical structure memory 13 stores the shapes and locations of the optic nerve N and neighboring anatomical structures of the optic nerve N, such as a vitreous body VB, a lens (crystalline lens) CB, and an optic nerve head H.

Examples of the anatomical structure memory 13 include recording media, such as an HDD (Hard Disc Drive), an SSD (Solid State Drive), an FD (Flexible Disc), an MO disc (Magneto-Optical disc), an MT (Magnetic Tape), a RAM (Random Access Memory), a CD (Compact Disc), a DVD (Digital Versatile Disc), an SD card (Secure Digital card), and a USB memory (Universal Serial Bus memory), and a server.

The optic nerve recognition unit 9 of the processor 19 performs image analysis on an ultrasound image acquired by the image acquisition unit 8 using the information stored in the anatomical structure memory 13 to recognize the optic nerve N of the subject and neighboring anatomical structures of the optic nerve N, such as the vitreous body VB. At this time, for example, the optic nerve recognition unit 9 uses the optic nerve N and its neighboring structures, which are stored in the anatomical structure memory 13, as a template, searches an image using the template to calculate a degree of similarity to the pattern data, and identifies the site to be recognized as being present in a location having a maximum degree of similarity greater than or equal to a threshold value to recognize the optic nerve N and its neighboring structures. The degree of similarity can be calculated using, as well as simple template matching, for example, a machine learning technique as described in Csurka et al.: Visual Categorization with Bags of Keypoints, Proc. of ECCV Workshop on Statistical Learning in Computer Vision, pp. 59-74 (2004), a typical image recognition technique based on deep learning as described in Krizhevsk et al.: ImageNet Classification with Deep Convolutional Neural Networks, Advances in Neural Information Processing Systems 25, pp. 1106-1114 (2012), or the like.

The optic nerve evaluation unit 10 of the processor 19 evaluates the shape, location, and the like of the optic nerve N of the subject recognized by the optic nerve recognition unit 9. At this time, the optic nerve evaluation unit 10 calculates evaluation values for the shape, location, and the like of the optic nerve N of the subject and compares the calculated evaluation values with threshold values stored in advance to evaluate the shape, location, and the like of the optic nerve N. For example, the optic nerve evaluation unit 10 can calculate, as an evaluation value for the shape of the optic nerve N of the subject, a degree of curvature C of the optic nerve N and compare the calculated degree of curvature C with a threshold degree of curvature Cth stored in advance to evaluate the shape of the optic nerve N.

The degree of curvature C is a measure of the degree to which the optic nerve N is curved. For example, the optic nerve evaluation unit 10 performs image analysis on the ultrasound image using the information stored in the anatomical structure memory 13 to calculate the degree of curvature C of the optic nerve N indicating the degree to which the center line extending in the length direction of the optic nerve N included in the ultrasound image is curved by using a typical shape of the optic nerve stored in the anatomical structure memory 13 as a reference. Alternatively, for example, the optic nerve evaluation unit 10 can perform image analysis on the ultrasound image to calculate the degree of curvature C of the optic nerve N by computing the curvature or the like of the center line extending along the length of the optic nerve N. Alternatively, for example, the optic nerve evaluation unit 10 can calculate, as the degree of curvature C of the optic nerve N, the degree of curvature of the center line extending in the length direction of the optic nerve N by using image analysis. Further, for example, the optic nerve evaluation unit 10 can calculate the angle of a central axis NA of the optic nerve N relative to the orientation of the ultrasound probe 18 as a slope S of the optic nerve N and compare the calculated slope S with a threshold slope Sth stored in advance to evaluate the location, shape, and the like of the optic nerve N.

The measurement unit 11 of the processor 19 performs measurement of the optic nerve N of the subject and its neighboring structures or the like from the ultrasound image on the basis of the recognition results obtained by the optic nerve recognition unit 9. For example, as illustrated in FIG. 4, the measurement unit 11 can measure the diameter of an optic nerve sheath NS from the ultrasound image. The measurement values measured from the ultrasound image, such as lengths, are generally used by a doctor or the like for the diagnosis of the subject and are desirably obtained as a result of measurement based on determined criteria. Accordingly, guidelines defining criteria for a measurement location, a measurement method, and the like for such measurement are generally known. The guidelines specify that, for example, in the case of measurement of the diameter of the optic nerve sheath NS, as illustrated in FIG. 4, a location that is a distance L of 3 mm away from the intersection of a retina R and the optic nerve sheath NS along the optic nerve N is determined as a measurement location, at which the diameter of the optic nerve sheath NS is measured. The measurement unit 11 measures the diameter of the optic nerve sheath NS in accordance with such guidelines, for example.

The reference data memory 14 of the ultrasound diagnostic apparatus 1 stores reference data regarding the optic nerves N, which is obtained when the optic nerve N of only one of the left and right eyes is curved with a degree of curvature greater than a determined degree of curvature and the degree of curvature of the optic nerve N of the other eye is smaller than the determined degree of curvature. For example, the reference data memory 14 can store, as reference data, measurement values collected from result data such as previous examination results obtained by the ultrasound diagnostic apparatus 1 or an external device. Like the anatomical structure memory 13, examples of the reference data memory 14 include recording media, such as an HDD, an SSD, an FD, an MO disc, an MT, a RAM, a CD, a DVD, an SD card, and a USB memory, and a server.

The operation guide unit 12 of the processor 19 guides the user to operate the ultrasound probe 18 so as to acquire an ultrasound image for measuring the optic nerve N of the subject on the basis of an evaluation result obtained by the optic nerve evaluation unit 10. If the degrees of curvature of both the left and right optic nerves N of the subject are larger than the determined degree of curvature, the operation guide unit 12 can estimate a measurement value of the optic nerve N on the basis of the reference data stored in the reference data memory 14. With the use of the operation guide unit 12, the ultrasound diagnostic apparatus 1 according to Embodiment 1 of the present invention can easily acquire an ultrasound image for measuring the optic nerve N of the subject, regardless of the user. The details will be described below.

The apparatus control unit 15 of the processor 19 controls each unit of the ultrasound diagnostic apparatus 1 in accordance with a program stored in the storage unit 17 or the like in advance and in accordance with the user's operation through the operating unit 16.

The display control unit 6 of the processor 19 performs, under control of the apparatus control unit 15, predetermined processing on the B-mode image and the like generated by the image generation unit 5 of the image acquisition unit 8 and causes the display unit 7 to display the B-mode image and the like.

The display unit 7 of the ultrasound diagnostic apparatus 1 displays an image and the like under control of the display control unit 6. The display unit 7 includes, for example, a display device such as an LCD (Liquid Crystal Display).

The operating unit 16 of the ultrasound diagnostic apparatus 1, which allows the user to perform an input operation, is configured to include a keyboard, a mouse, a trackball, a touchpad, a touch panel, and the like.

The storage unit 17 stores an operation program and the like for the ultrasound diagnostic apparatus 1. Like the anatomical structure memory 13 and the reference data memory 14 of the ultrasound diagnostic apparatus 1, examples of the storage unit 17 include recording media, such as an HDD, an SSD, an FD, an MO disc, an MT, a RAM, a CD, a DVD, an SD card, and a USB memory, and a server.

The processor 19 having the display control unit 6, the image acquisition unit 8, the optic nerve recognition unit 9, the optic nerve evaluation unit 10, the measurement unit 11, the operation guide unit 12, and the apparatus control unit 15 is constituted by a CPU (Central Processing Unit) and a control program for causing the CPU to perform various processing operations, or may be configured using a digital circuit. The display control unit 6, the image acquisition unit 8, the optic nerve recognition unit 9, the optic nerve evaluation unit 10, the measurement unit 11, the operation guide unit 12, and the apparatus control unit 15 may be integrally constituted by configured to be partially or entirely integrated into a single CPU.

Next, the operation of the ultrasound diagnostic apparatus 1 according to Embodiment 1 will be described in detail with reference to a flowchart illustrated in FIG. 5.

First, in step S1, the image acquisition unit 8 acquires an ultrasound image including the optic nerve N of the subject. At this time, for example, the user brings the ultrasound probe 18 into contact with one of the left and right eyelids of the subject, while the eyes of the subject are closed. In this state, the image acquisition unit 8 transmits ultrasound waves toward the optic nerve N of the subject via the vibrator array 2 of the ultrasound probe 18, and acquires an ultrasound image in response to receipt of ultrasound echoes reflected from the optic nerve N of the subject and its neighboring structures.

Then, in step S2, the optic nerve recognition unit 9 performs image analysis on the ultrasound image acquired in step S1 using the information stored in the anatomical structure memory 13 to recognize the optic nerve N and its neighboring anatomical structures.

In step S3, the optic nerve evaluation unit 10 calculates evaluation values for the shape, location, and the like of the optic nerve N of the subject on the basis of the optic nerve N of the subject and its neighboring structures, which are recognized by the optic nerve recognition unit 9. At this time, the optic nerve evaluation unit 10 calculates, as evaluation values for the optic nerve N, the degree of curvature C of the optic nerve N of the subject and the angle of the central axis NA of the optic nerve N relative to the orientation of the ultrasound probe 18 as the slope S of the optic nerve N.

In step S4, the optic nerve evaluation unit 10 determines whether the degree of curvature C of the optic nerve N calculated in step S3 is greater than the threshold degree of curvature Cth. If the degree of curvature C of the optic nerve N calculated in step S3 is less than or equal to the threshold degree of curvature Cth, the process proceeds to step S5.

In step S5, the optic nerve evaluation unit 10 determine whether the slope S of the optic nerve N calculated in step S3 is larger than the threshold slope Sth. If the slope S of the optic nerve N calculated in step S3 is less than or equal to the threshold slope Sth, the process proceeds to step S6.

In step S6, the measurement unit 11 performs measurement of the optic nerve N from the ultrasound image acquired in step S1. For example, the measurement unit 11 can measure the diameter of the optic nerve sheath NS from the ultrasound image in accordance with criteria defined in guidelines or the like.

Then, in step S7, the operation guide unit 12 displays a measurement result obtained by the measurement unit 11 on the display unit 7 via the display control unit 6.

Figure 6:
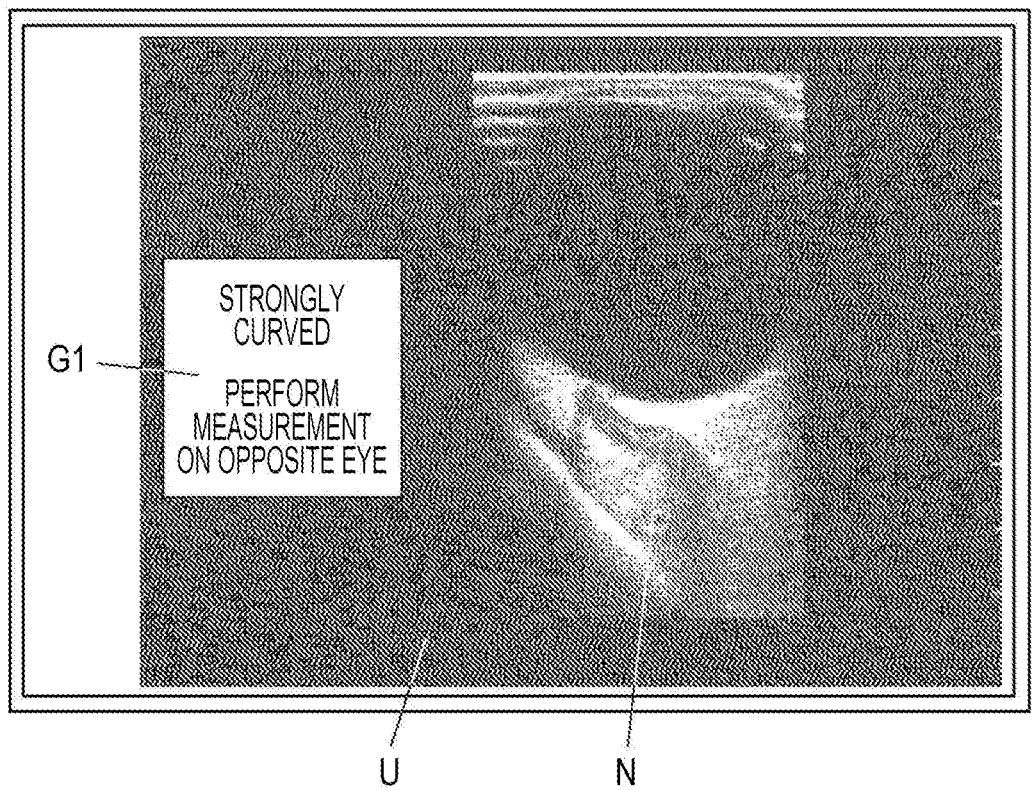
FIG. 6 is a diagram illustrating an example of a guide marker in Embodiment 1 of the present invention.

If the optic nerve evaluation unit 10 determines in step S4 that the degree of curvature C of the optic nerve N calculated in step S3 is greater than the threshold degree of curvature Cth, the process proceeds to step S8. In step S8, the operation guide unit 12 guides the user to operate the ultrasound probe 18 so as to measure the eye opposite to the eye for which the ultrasound image is acquired in step S1. For example, as illustrated in FIG. 6, the operation guide unit 12 displays, on the display unit 7 together with an ultrasound image U, a guide marker G1 for informing the user that the optic nerve N is greatly curved and for guiding the user to perform measurement on the opposite eye.

Then, in step S9, an ultrasound image including the optic nerve N of the eye for which measurement is guided in step S4 is acquired through processing similar to that of step S1.

In step S10, as in the processing of step S2, the optic nerve recognition unit 9 performs image analysis on the ultrasound image acquired in step S9 using the information stored in the anatomical structure memory 13 to recognize the optic nerve N of the subject and its neighboring anatomical structures.

Then, in step S11, as in the processing of step S3, the optic nerve evaluation unit 10 calculates the degree of curvature C as an evaluation value for the optic nerve N on the basis of the recognition result obtained by the optic nerve recognition unit 9.

In step S12, as in the processing of step S4, the optic nerve evaluation unit 10 determines whether the degree of curvature C calculated in step S11 is greater than the threshold degree of curvature Cth. If the degree of curvature C is less than or equal to the threshold degree of curvature Cth, the process proceeds to step S13.

In step S13, as in the processing of step S6, the measurement unit 11 performs measurement of the optic nerve N. Then, in step S14, the operation guide unit 12 displays a measurement result of the optic nerve N obtained in step S13 on the display unit 7.

If the optic nerve evaluation unit 10 determines in step S12 that the degree of curvature C of the optic nerve N is greater than the threshold degree of curvature Cth, the process proceeds to step S15.

In step S15, the measurement unit 11 performs measurement of the left and right optic nerves N of the subject using the ultrasound image acquired in step S1 or the ultrasound image acquired in step S9.

Then, in step S16, the operation guide unit 12 estimates a measurement value for the case where the optic nerve of the subject is not greatly curved, that is, for the case where the degree of curvature C of the optic nerve N is assumed to be less than or equal to the threshold degree of curvature Cth, on the basis of the measurement values of the left and right optic nerves N of the subject, which are obtained by the measurement unit 11, and on the basis of the reference data stored in the reference data memory 14, and displays the estimated measurement result on the display unit 7.

It is known that, for example, when the degree of curvature C of the optic nerve N of one of the left and right eyes of the subject is greater than the threshold degree of curvature Cth and the degree of curvature C of the optic nerve N of the other eye is less than or equal to the threshold degree of curvature Cth, a correlation exists between the diameter of the optic nerve sheath NS of the optic nerve N for which the degree of curvature C is greater than the threshold degree of curvature Cth and the diameter of the optic nerve sheath NS of the optic nerve N for which the degree of curvature C is less than or equal to the threshold degree of curvature Cth. The operation guide unit 12 can use such a correlation to estimate a measurement value for the diameter of the optic nerve sheath NS. Specifically, for example, the reference data memory 14 stores a regression line RL illustrated in FIG. 7 as reference data. When the diameter of the optic nerve sheath NS of the subject is to be measured, the operation guide unit 12 can estimate a measurement value for the case where the degree of curvature C of the optic nerve N is less than or equal to the threshold degree of curvature Cth, on the basis of the diameter of the optic nerve sheath NS calculated by the measurement unit 11 using the ultrasound image acquired in step S1 or step S9 and on the basis of the regression line RL stored in the reference data memory 14.

The reference data memory 14 may store, instead of the regression line RL, a formula representing a correlation between the optic nerve sheath diameter of a curved optic nerve and the optic nerve sheath diameter of a non-curved optic nerve or a table regarding measurement values for the optic nerve sheath diameter of a curved optic nerve and the optic nerve sheath diameter of a non-curved optic nerve.

The operation guide unit 12 may estimate a measurement value on the basis of the regression line RL by using the average value of the diameters of the optic nerve sheath NS measured by the measurement unit 11 using the ultrasound images acquired in steps S1 and S9.

Figure 7:
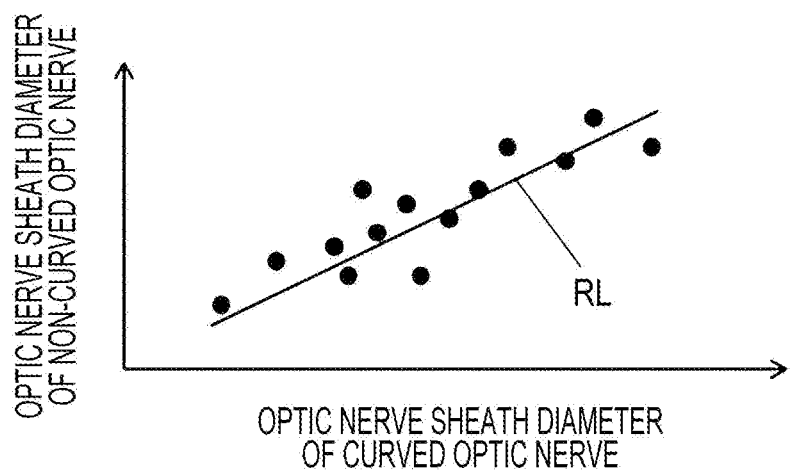
FIG. 7 is a diagram illustrating an example regression line obtained from previous result data.

In the graph illustrated in FIG. 7, the diameters of the left and right optic nerve sheaths NS, which are measured when the degree of curvature C of the optic nerve N of one of the left and right eyes is greater than the threshold degree of curvature Cth and the degree of curvature C of the optic nerve N of the other eye is less than or equal to the threshold degree of curvature Cth during a plurality of diagnoses conducted in the past, are plotted as the optic nerve sheath diameter of the curved optic nerve and the optic nerve sheath diameter of the non-curved optic nerve. Based on these multiple plots, the regression line RL indicating the correlation between the optic nerve sheath diameter of the curved optic nerve and the optic nerve sheath diameter of the non-curved optic nerve is obtained.

Figure 8:
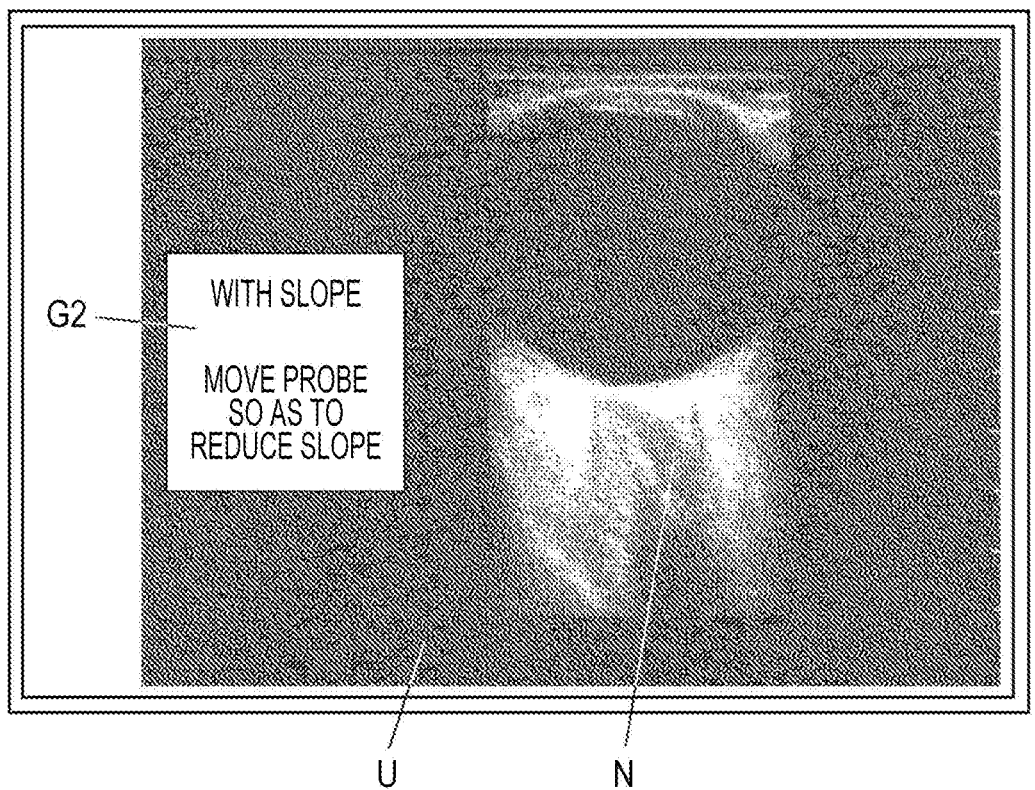
FIG. 8 is a diagram illustrating another example of the guide marker in Embodiment 1 of the present invention.

If the optic nerve evaluation unit 10 determines in step S5 that the slope S of the optic nerve N is larger than the threshold slope Sth, the process proceeds to step S17. In step S17, the operation guide unit 12 guides the user to operate the ultrasound probe 18 so as to reduce the slope S of the optic nerve N of the subject. For example, as illustrated in FIG. 8, the operation guide unit 12 can display, on the display unit 7 together with the ultrasound image U, a guide marker G2 for informing the user that the optic nerve N is largely tilted and guiding the user to move the ultrasound probe 18 so as to reduce the slope S.

When the operation guide unit 12 provides the user with a guide in step S17, the process returns to step S1. In step S1, the user operates the ultrasound probe 18 so as to reduce the slope S of the optic nerve N in accordance with the guide provided by the operation guide unit 12, and, in this state, the image acquisition unit 8 acquires an ultrasound image. Then, in steps S2 and S3, the recognition of the optic nerve N and the calculation of the evaluation values for the optic nerve N are performed. If it is determined in step S4 that the degree of curvature C of the optic nerve N is less than or equal to the threshold degree of curvature Cth, the process proceeds to step S5. Further, if it is determined that the slope S of the optic nerve N is larger than the threshold slope Sth, the process proceeds to step S17. In this way, the processing of steps S1 to S5 and S17 is repeatedly performed until the optic nerve evaluation unit 10 determines that the slope S of the optic nerve N is less than or equal to the threshold slope Sth.

If it is determined in step S4 that the degree of curvature C of the optic nerve N is greater than the threshold degree of curvature Cth, the processing of steps S8 to S12 is performed and, then, the processing of steps S13 and S14 or the processing of steps S15 and S16 is performed. Then, the operation of the ultrasound diagnostic apparatus 1 ends. If it is determined in step S5 that the slope S of the optic nerve N is less than or equal to the threshold slope Sth, the processing of steps S6 and S7 is performed. Then, the operation of the ultrasound diagnostic apparatus 1 ends.

As described above, the ultrasound diagnostic apparatus 1 according to Embodiment 1 of the present invention guides the user to operate the ultrasound probe 18 so as to acquire an ultrasound image for measuring the optic nerve N of the subject on the basis of the evaluation result obtained by the optic nerve evaluation unit 10. Accordingly, an ultrasound image suitable for measuring the optic nerve N can be acquired, regardless of the user's skill, and accurate measurement can be performed. In addition, for example, even if the left and right optic nerves N are greatly curved and it is difficult to acquire an ultrasound image suitable for measuring the optic nerves N, a measurement value for the case where the degree of curvature C of the optic nerve N is small is estimated. Accordingly, an accurate measurement result can be obtained, regardless of the user.

In Embodiment 1, the transmitting unit 3 and the receiving unit 4 are included in the image acquisition unit 8 of the processor 19. Alternatively, the transmitting unit 3 and the receiving unit 4 may be included in the ultrasound probe 18. In this case, the transmitting unit 3 and the receiving unit 4 included in the ultrasound probe 18 and the image generation unit 5 included in the processor 19 constitute the image acquisition unit 8.

In Embodiment 1, the anatomical structure memory 13 may be included in the optic nerve recognition unit 9 and the optic nerve evaluation unit 10. Even in this case, as in the manner described in Embodiment 1, the optic nerve recognition unit 9 can use information regarding neighboring anatomical structures of the optic nerve N of the subject to recognize the optic nerve N and its neighboring anatomical structures. In addition, as in the manner described in Embodiment 1, the optic nerve evaluation unit 10 can also use information regarding neighboring anatomical structures of the optic nerve N of the subject to perform evaluation for the shape, location, and the like of the optic nerve N.

Depending on the location and orientation of the ultrasound probe 18 operated by the user, the retina R and the optic nerve N may not sometimes be seen to be connected to each other in an ultrasound image. For example, to measure the diameter of the optic nerve sheath NS, an ultrasound image in which the retina R and the optic nerve N appear not to be connected to each other is not suitable as an ultrasound image to measure the diameter of the optic nerve sheath NS since suitable measurement locations, as defined in the guidelines, are not identifiable in the ultrasound image. Accordingly, in order to be capable of acquiring an ultrasound image suitable for measuring the optic nerve N, the optic nerve evaluation unit 10 may evaluate whether the retina R and the optic nerve N are connected to each other in the ultrasound image.

At this time, for example, immediately after the optic nerve N is recognized in step S2, the optic nerve evaluation unit 10 can determine whether the retina R and the optic nerve N are connected to each other in the ultrasound image. If the optic nerve evaluation unit 10 determines that the retina R and the optic nerve N are connected to each other in the ultrasound image, the process can proceed to step S3. Then, the optic nerve evaluation unit 10 can calculate evaluation values for the optic nerve N and perform the subsequent steps. For example, if the optic nerve evaluation unit 10 determines that the retina R and the optic nerve N are not connected to each other in the ultrasound image, the operation guide unit 12 can guide the user to operate the ultrasound probe 18 so as to acquire an ultrasound image in which the retina R and the optic nerve N are connected to each other. In this manner, guiding the user to operate the ultrasound probe 18 on the basis of not only the degree of curvature C and the slope S of the optic nerve N but also whether the retina R and the optic nerve N are connected to each other allows acquisition of a more suitable ultrasound image for measuring the optic nerve N, and can improve measurement accuracy.

When guiding the user to operate the ultrasound probe 18, the operation guide unit 12 may display the evaluation values calculated by the optic nerve evaluation unit 10 on the display unit 7. For example, the operation guide unit 12 can display on the display unit 7 the degree of curvature C and the slope S of the optic nerve N and whether the retina R and the optic nerve N are connected to each other in an ultrasound image. This allows the user to operate the ultrasound probe 18 while referring to specific evaluation values.

In addition, when guiding the user to operate the ultrasound probe 18, the operation guide unit 12 can also display on the display unit 7 a measurement result of the optic nerve N based on the currently acquired ultrasound image. In this case, for example, during a period from when the optic nerve N and its neighboring structures are recognized in step S2 to when the degree of curvature C of the optic nerve N is evaluated in step S4, the diameter of the optic nerve sheath NS recognized in step S2 is measured by the measurement unit 11, and the operation guide unit 12 displays a measurement result on the display unit 7. The measurement result of the optic nerve N can include, for example, a measurement value, a measurement line used for measurement, calipers, and so on. In this manner, displaying a measurement result of the optic nerve N on the display unit 7 when providing the user with a guide allows the user to recognize that suitable measurement is not being performed on the currently acquired ultrasound image, and can prompt the user to operate the ultrasound probe 18.

In addition, when guiding the user to operate the ultrasound probe 18, the operation guide unit 12 can present, using an ultrasound image, the optic nerve N and its neighboring anatomical structures in the currently acquired ultrasound image. For example, although not illustrated, the operation guide unit 12 can superimpose the contour of the optic nerve N and its neighboring anatomical structures recognized in step S2 and colored portions or the like representing the optic nerve N and its neighboring anatomical structures on the ultrasound image and display the resulting ultrasound image on the display unit 7. Accordingly, a user who is unlikely to be able to determine the optic nerve N and its neighboring anatomical structures by visually checking an ultrasound image, for example, a user who is unfamiliar with ultrasound diagnosis, can easily recognize that the optic nerve N is curved in the ultrasound image and that the optic nerve N is tilted.

In addition, in step S17, the operation guide unit 12 guides the user to operate the ultrasound probe 18 so as to reduce the slope S of the optic nerve N. Alternatively, the operation guide unit 12 can present to the user a specific amount of movement, a specific amount of rotation, and the like of the ultrasound probe 18 to reduce the slope S of the optic nerve N.

For example, although not illustrated, the ultrasound diagnostic apparatus 1 is provided with a probe operation-amount calculation unit that calculates the amount of movement, the amount of rotation, such as yaw angle, and the like of the ultrasound probe 18 to reduce the slope S of the optic nerve N, on the basis of the image analysis result obtained by the optic nerve recognition unit 9 and on the basis of the optic nerve N and its neighboring anatomical structures stored in the anatomical structure memory 13. Accordingly, the operation guide unit 12 can display a specific amount of movement, a specific amount of rotation, and the like of the ultrasound probe 18, which are calculated by the probe operation-amount calculation unit, on the display unit 7.

More specifically, for example, the probe operation-amount calculation unit can cause the image acquisition unit 8 to acquire ultrasound images of a plurality of frames including in a time series ultrasound images that has been subjected to evaluation by the optic nerve evaluation unit 10, and can calculate the amount of movement, the amount of rotation, and the like of the ultrasound probe 18 on the basis of the recognition results obtained by the optic nerve recognition unit 9 for the ultrasound images of the plurality of frames and on the basis of the optic nerve N and its neighboring anatomical structures stored in the anatomical structure memory 13. This allows the user to operate the ultrasound probe 18 while referring to the specific amount of movement and the specific amount of rotation of the ultrasound probe 18. Accordingly, an ultrasound image suitable for measuring the optic nerve N can be more easily acquired.

Further, for example, although not illustrated, the ultrasound probe 18 can be provided with an attitude angle detection sensor configured to include a sensor such as an acceleration sensor, a gyro-sensor, a magnetic sensor, or a GPS (Global Positioning System) sensor. In this case, the operation guide unit 12 can display a specific amount of movement, a specific amount of rotation, and the like of the ultrasound probe 18, which are calculated by the probe operation-amount calculation unit, on the display unit 7.

In Embodiment 1, furthermore, the reference data memory 14 stores the regression line RL indicating the correlation between the optic nerve sheath diameter of a curved optic nerve and the optic nerve sheath diameter of a non-curved optic nerve. Alternatively, the reference data memory 14 may store an object, other than the regression line RL, indicating the correlation between the measurement value of a curved optic nerve and the measurement value of a non-curved optic nerve. For example, when a regression curve is obtained from the multiple plots illustrated in FIG. 7, the reference data memory 14 can store the regression curve as reference data. At this time, the operation guide unit 12 can estimate, based on the regression curve, a measurement value for the case where the degree of curvature C of the optic nerve N is less than or equal to the threshold degree of curvature Cth, from the optic nerve sheath diameter of a curved optic nerve for which the degree of curvature C is greater than the threshold degree of curvature Cth.

Furthermore, in step S16, the operation guide unit 12 estimates a measurement value for the case where the degree of curvature C of the optic nerve N is less than or equal to the threshold degree of curvature Cth, using the regression line RL stored in the reference data memory 14. Alternatively, the operation guide unit 12 may use machine learning based on an image feature value to estimate a measurement value for the case where the degree of curvature C of the optic nerve N is less than or equal to the threshold degree of curvature Cth. For example, a learning model that has learned to output an optic nerve sheath diameter of a non-curved optic nerve for which the degree of curvature C is less than or equal to the threshold degree of curvature Cth in response to input of an optic nerve sheath diameter of a curved optic nerve for which the degree of curvature C is greater than the threshold degree of curvature Cth by using a method for deep learning may be stored in the reference data memory 14. In this case, the operation guide unit 12 can use the learning model to estimate a measurement value for the case where the degree of curvature C of the optic nerve N is less than or equal to the threshold degree of curvature Cth, from the optic nerve sheath diameter of the curved optic nerve for which the degree of curvature C is greater than the threshold degree of curvature Cth.

Alternatively, in step S16, the operation guide unit 12 can, instead of estimating a measurement value for the case where the degree of curvature C of the optic nerve N is less than or equal to the threshold degree of curvature Cth, display an error on the display unit 7 to terminate the operation of the ultrasound diagnostic apparatus 1. In this case, the ultrasound diagnostic apparatus 1 does not need to include the reference data memory 14. Alternatively, at this time, the operation guide unit 12 may display the measurement result obtained by the measurement unit 11 on the display unit 7.

In Embodiment 1, furthermore, the operation guide unit 12 guides the user to operate the ultrasound probe 18 by using display on the display unit 7. Alternatively, the operation guide unit 12 may guide the user to operate the ultrasound probe 18 by using audio. For example, although not illustrated, the ultrasound diagnostic apparatus 1 may be provided with an audio generation unit configured to include a speaker and the like. Accordingly, the operation guide unit 12 can guide the user to operate the ultrasound probe 18 by using audio generated from the audio generation unit.

In Embodiment 1, furthermore, the measurement unit 11 automatically calculates a measurement value for the optic nerve N. The measurement unit 11 can calculate a measurement value manually in accordance with an operation by the user through the operating unit 16. For example, when the user places a measurement line and a pair of calipers or the like for measuring a length on the ultrasound image using the operating unit 16, the measurement unit 11 can measure the length of the placed measurement line, the length between the pair of calipers, and the like.

Embodiment 2

Figure 9:
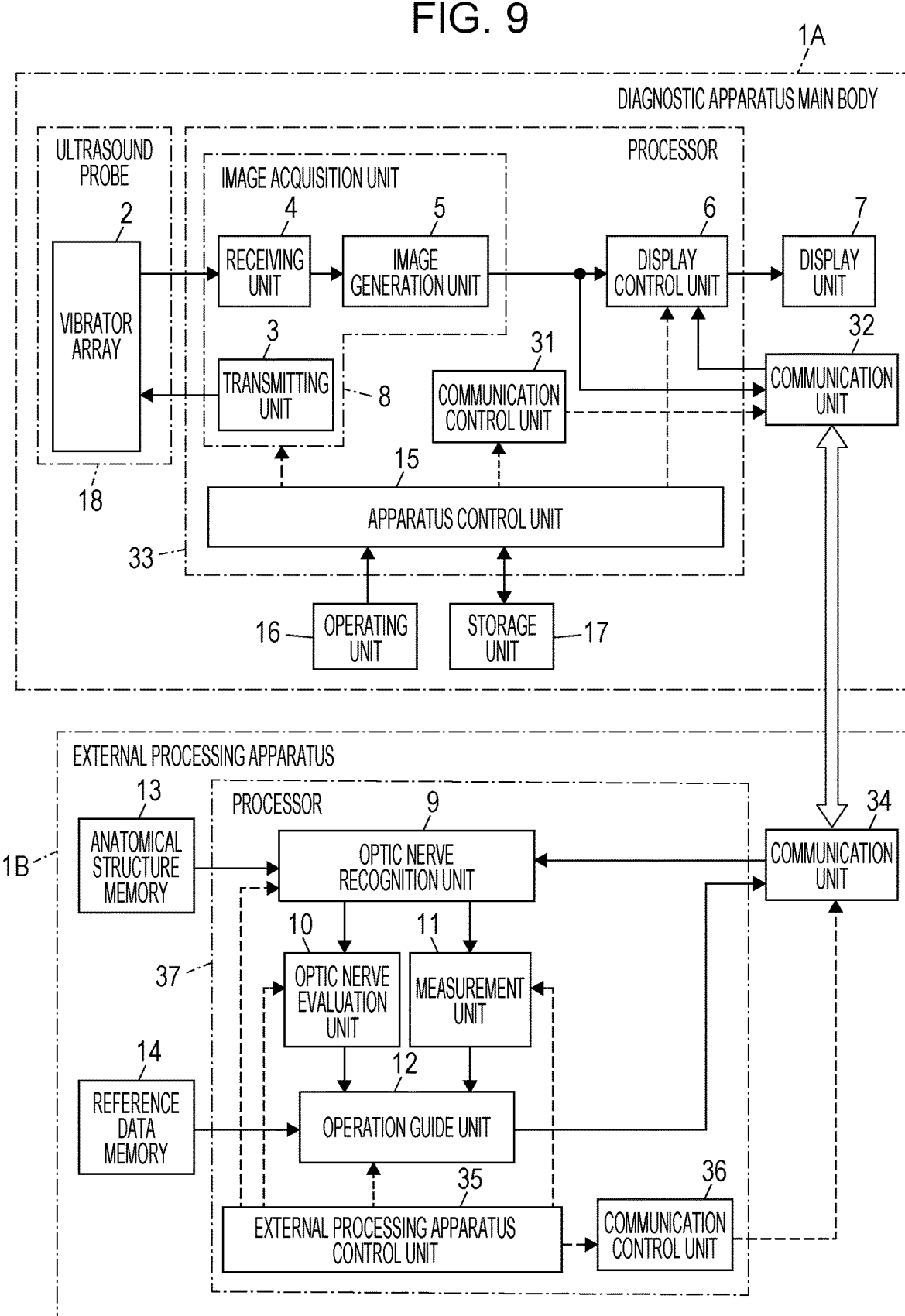
FIG. 9 is a block diagram illustrating a configuration of an ultrasound diagnostic apparatus according to Embodiment 2 of the present invention.

FIG. 9 illustrates a configuration of an ultrasound diagnostic apparatus according to Embodiment 2 of the present invention. The ultrasound diagnostic apparatus according to Embodiment 2 includes a diagnostic apparatus main body 1A and an external processing apparatus 1B, which are interactively connected to each other via communication.

The diagnostic apparatus main body 1A includes the vibrator array 2 of the ultrasound probe 18, and the vibrator array 2 is connected to the transmitting unit 3 and the receiving unit 4. The receiving unit 4 is sequentially connected to the image generation unit 5, the display control unit 6, and the display unit 7. The transmitting unit 3, the receiving unit 4, and the image generation unit 5 constitute the image acquisition unit 8.

The display control unit 6 and the image acquisition unit 8 are further connected to the apparatus control unit 15, and the apparatus control unit 15 is connected to the operating unit 16 and the storage unit 17. The apparatus control unit 15 and the storage unit 17 are connected so as to enable two-way exchange of information.

The apparatus control unit 15 is further connected to a communication control unit 31, and the image generation unit 5 and the communication control unit 31 are connected to a communication unit 32.

The display control unit 6, the image acquisition unit 8, the apparatus control unit 15, and the communication control unit 31 constitute a processor 33.

The external processing apparatus 1B has a communication unit 34. The communication unit 34 is connected to the optic nerve recognition unit 9, and the optic nerve recognition unit 9 is connected to the optic nerve evaluation unit 10, the measurement unit 11, and the anatomical structure memory 13. The optic nerve evaluation unit 10 and the measurement unit 11 are further connected to the operation guide unit 12, and the operation guide unit 12 is connected to the communication unit 34 and the reference data memory 14.

The optic nerve recognition unit 9, the optic nerve evaluation unit 10, the measurement unit 11, and the operation guide unit 12 are connected to an external processing apparatus control unit 35, and the external processing apparatus control unit 35 is connected to the communication unit 34 via a communication control unit 36.

The optic nerve recognition unit 9, the optic nerve evaluation unit 10, the measurement unit 11, the operation guide unit 12, the external processing apparatus control unit 35, and the communication control unit 36 constitute a processor 37.

The display control unit 6, the image acquisition unit 8, the apparatus control unit 15, the operating unit 16, the storage unit 17, and the ultrasound probe 18 of the diagnostic apparatus main body 1A, and the optic nerve recognition unit 9, the optic nerve evaluation unit 10, the measurement unit 11, the operation guide unit 12, the anatomical structure memory 13, and the reference data memory 14 of the external processing apparatus 1B are the same as those in the ultrasound diagnostic apparatus 1 of Embodiment 1.

The communication control unit 31 of the diagnostic apparatus main body 1A controls the communication unit 32 to transmit an ultrasound image generated by the image generation unit 5 of the image acquisition unit 8 and to receive a measurement result and operation guide transmitted from the external processing apparatus 1B.

The external processing apparatus control unit 35 of the external processing apparatus 1B controls each unit of the external processing apparatus 1B.

The communication control unit 36 of the external processing apparatus 1B controls the communication unit 34 to receive the ultrasound image transmitted from the diagnostic apparatus main body 1A and to transmit a measurement result obtained by the measurement unit 11 and an operation guide obtained by the operation guide unit 12.

That is, the ultrasound diagnostic apparatus according to Embodiment 2 is configured such that, in the ultrasound diagnostic apparatus 1 of Embodiment 1 illustrated in FIG. 1, the diagnostic apparatus main body 1A including the ultrasound probe 18, the image acquisition unit 8, the display control unit 6, and the display unit 7 to acquire and display an ultrasound image, and the external processing apparatus 1B including the optic nerve recognition unit 9, the optic nerve evaluation unit 10, the measurement unit 11, the operation guide unit 12, the anatomical structure memory 13, and the reference data memory 14 to measure the optic nerve on the basis of the ultrasound image and to implement an operation guide are connected via communication between the communication units 32 and 34.

The processor 33 of the diagnostic apparatus main body 1A and the processor 37 of the external processing apparatus 1B are each constituted by a CPU and a control program for causing the CPU to perform various processing operations, or may be each constituted by using a digital circuit.

In the ultrasound diagnostic apparatus according to Embodiment 2, an ultrasound image acquired by the image acquisition unit 8 of the diagnostic apparatus main body 1A is displayed on the display unit 7 via the display control unit 6, and the ultrasound image is transmitted to the communication unit 34 of the external processing apparatus 1B through the communication unit 32 via communication. The ultrasound image received by the communication unit 34 of the external processing apparatus 1B is sent to the optic nerve recognition unit 9 and is subjected to image analysis by the optic nerve recognition unit 9 to recognize the optic nerve N and its neighboring anatomical structures. Further, the optic nerve evaluation unit 10 calculates evaluation values for the shape, location, and the like of the optic nerve N, and the measurement unit 11 performs measurement for the optic nerve N. A measurement result obtained by the measurement unit 11 is sent to the communication unit 34 through the operation guide unit 12 and is transmitted from the communication unit 34 to the diagnostic apparatus main body 1A. The measurement result received by the communication unit 32 of the diagnostic apparatus main body 1A is displayed on the display unit 7 via the display control unit 6.

The operation guide, which is obtained by the operation guide unit 12 in accordance with the evaluation values calculated by the optic nerve evaluation unit 10 of the external processing apparatus 1B, is also transmitted from the communication unit 34 to the diagnostic apparatus main body 1A, and the operation guide received by the communication unit 32 of the diagnostic apparatus main body 1A is displayed on the display unit 7 via the display control unit 6.

Figure 5:
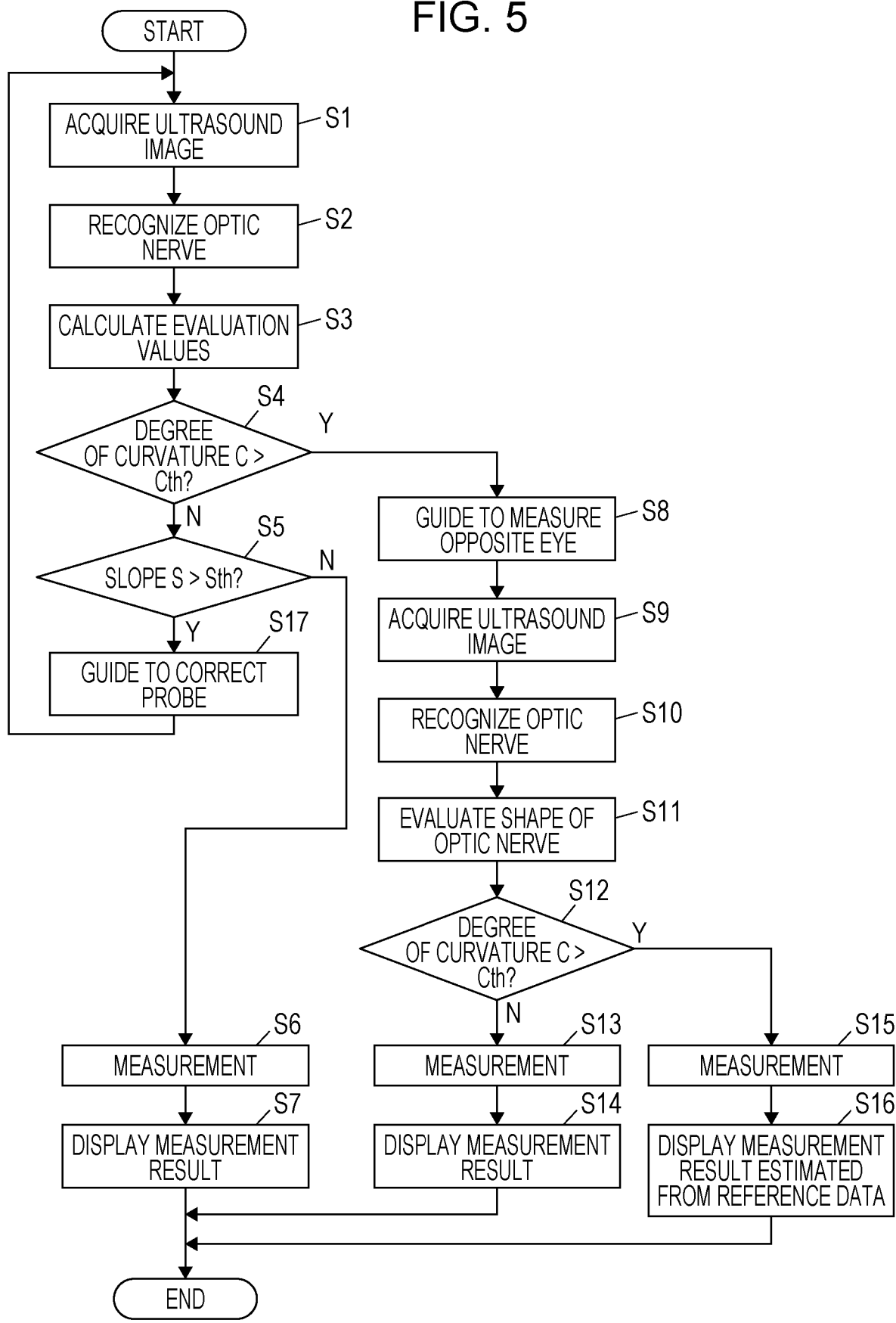
FIG. 5 is a flowchart illustrating the operation of the ultrasound diagnostic apparatus according to Embodiment 1 of the present invention.

In the ultrasound diagnostic apparatus according to Embodiment 2, accordingly, the same operation as the operation according to Embodiment 1 illustrated in the flowchart in FIG. 5 can be performed while communication takes place between the diagnostic apparatus main body 1A and the external processing apparatus 1B.

With the connection between the diagnostic apparatus main body 1A and the external processing apparatus 1B via communication, even if the diagnostic apparatus main body 1A that acquires an ultrasound image has low processing capabilities, information on the ultrasound image acquired by the diagnostic apparatus main body 1A is transmitted to the external processing apparatus 1B such that the evaluation and measurement of the optic nerve N can be performed by the external processing apparatus 1B. Accordingly, the ultrasound diagnostic apparatus according to Embodiment 2 is suitable for medical treatment in a remote place, for example.

The communication between the diagnostic apparatus main body 1A and the external processing apparatus 1B may be any of various types of communication such as network-based communication and wireless communication.

REFERENCE SIGNS LIST 1 ultrasound diagnostic apparatus
1A diagnostic apparatus main body
1B external processing apparatus
2 vibrator array
3 transmitting unit
4 receiving unit
5 image generation unit
6 display control unit
7 display unit
8 image acquisition unit
9 optic nerve recognition unit
10 optic nerve evaluation unit
11 measurement unit 12 operation guide unit
13 anatomical structure memory
14 reference data memory
15 apparatus control unit
16 operating unit
17 storage unit
18 ultrasound probe
19, 33, 37 processor
20 amplification unit
21 AD conversion unit
22 signal processing unit
23 DSC
24 image processing unit
31, 36 communication control unit
32, 34 communication unit
35 external processing apparatus control unit
CB lens
EA eyeball axis
G1, G2 guide marker
H optic nerve head
L distance
N optic nerve
NA central axis
NS optic nerve sheath
R retina
RL regression line
S slope
U ultrasound image
VB vitreous body

What is claimed is:

1. An ultrasound diagnostic apparatus comprising a processor configured to:
   transmit an ultrasound beam from an ultrasound probe to a subject to acquire an ultrasound image;
   perform image analysis on the acquired ultrasound image to recognize an optic nerve of the subject;
   evaluate whether the optic nerve of the subject is curved with a degree of curvature greater than a determined degree of curvature; and
   guide a user to operate the ultrasound probe so as to acquire an ultrasound image for measurement of the optic nerve of the subject and perform measurement on an opposite eye, when the optic nerve of the subject is evaluated to be curved with a degree of curvature greater than the determined degree of curvature.

2. The ultrasound diagnostic apparatus according to claim 1, further comprising
   a reference data memory that stores reference data regarding an optic nerve of only one of left and right eyes that is curved with a degree of curvature greater than the determined degree of curvature,
   wherein when an optic nerve of the opposite eye is evaluated to be curved with a degree of curvature greater than the determined degree of curvature, the processor presents to the user a measurement result of the optic nerve of the subject, the measurement result being estimated on the basis of the reference data stored in the reference data memory.

3. The ultrasound diagnostic apparatus according to claim 2,
   wherein the reference data memory stores the reference data that is collected from previous result data.

4. The ultrasound diagnostic apparatus according to claim 3,
   wherein the processor estimates a measurement result obtained assuming that the degree of curvature of the optic nerve of the subject is less than or equal to the determined degree of curvature, by using a regression line obtained from the previous result data.

5. The ultrasound diagnostic apparatus according to claim 2,
   wherein the processor estimates the measurement result of the optic nerve of the subject through machine learning using an image feature value.

6. The ultrasound diagnostic apparatus according to claim 1,
   wherein when the degree of curvature of the optic nerve of the subject is evaluated to be less than or equal to the determined degree of curvature, the processor further evaluates whether the optic nerve of the subject is tilted with a slope greater than a determined slope.

7. The ultrasound diagnostic apparatus according to claim 2,
   wherein when the degree of curvature of the optic nerve of the subject is evaluated to be less than or equal to the determined degree of curvature, the processor further evaluates whether the optic nerve of the subject is tilted with a slope greater than a determined slope.

8. The ultrasound diagnostic apparatus according to claim 3,
   wherein when the degree of curvature of the optic nerve of the subject is evaluated to be less than or equal to the determined degree of curvature, the processor further evaluates whether the optic nerve of the subject is tilted with a slope greater than a determined slope.

9. The ultrasound diagnostic apparatus according to claim 4,
   wherein when the degree of curvature of the optic nerve of the subject is evaluated to be less than or equal to the determined degree of curvature, the processor further evaluates whether the optic nerve of the subject is tilted with a slope greater than a determined slope.

10. The ultrasound diagnostic apparatus according to claim 5,
    wherein when the degree of curvature of the optic nerve of the subject is evaluated to be less than or equal to the determined degree of curvature, the processor further evaluates whether the optic nerve of the subject is tilted with a slope greater than a determined slope.

11. The ultrasound diagnostic apparatus according to claim 6,
    wherein when the degree of curvature of the optic nerve of the subject is evaluated to be less than or equal to the determined degree of curvature and the optic nerve of the subject is evaluated to be tilted with a slope greater than the determined slope, the processor guides the user to operate the ultrasound probe so as to reduce the slope of the optic nerve of the subject.

12. The ultrasound diagnostic apparatus according to claim 7,
    wherein when the degree of curvature of the optic nerve of the subject is evaluated to be less than or equal to the determined degree of curvature and the optic nerve of the subject is evaluated to be tilted with a slope greater than the determined slope, the processor guides the user to operate the ultrasound probe so as to reduce the slope of the optic nerve of the subject.

13. The ultrasound diagnostic apparatus according to claim 1, further comprising:
    a diagnostic apparatus main body having the ultrasound probe and a first processor that acquires the ultrasound image; and
    an external processing apparatus having a second processor that recognizes the optic nerve of the subject, evaluates the shape of the optic nerve of the subject, and guides the user to operate the ultrasound probe, wherein the diagnostic apparatus main body and the external processing apparatus are connected to each other via communication.

14. A method for controlling an ultrasound diagnostic apparatus, comprising:

transmitting an ultrasound beam from an ultrasound probe to a subject to acquire an ultrasound image;

performing image analysis on the acquired ultrasound image to recognize an optic nerve of the subject;

evaluating whether the optic nerve of the subject is curved with a degree of curvature greater than a determined degree of curvature; and guiding a user to operate the ultrasound probe so as to acquire an ultrasound image for measurement of the optic nerve of the subject and perform measurement on an opposite eye, when the optic nerve of the subject is evaluated to be curved with a degree of curvature greater than the determined degree of curvature.

* * * * *